US005985627A

United States Patent [19]
Mortensen et al.

[11] Patent Number: 5,985,627
[45] Date of Patent: Nov. 16, 1999

[54] MODIFIED CARBOXYPEPTIDASE

[75] Inventors: Uffe Mortensen, København S; Kjeld Olesen, Frederiksberg, both of Denmark; Henning Stennicke, San Diego, Calif.; Steen B. Sørensen, Solrødstrand; Klaus Breddam, Roskilde, both of Denmark

[73] Assignee: Carlsberg Laboratory, Copenhagen Valby, Denmark

[21] Appl. No.: 08/807,263

[22] Filed: Feb. 28, 1997

[51] Int. Cl.⁶ .............................. C12P 13/02; C12N 9/14; C12N 9/48
[52] U.S. Cl. .................. 435/129; 435/195; 435/212; 435/223; 435/224; 435/440; 530/402
[58] Field of Search .................................. 435/195, 212, 435/223, 224, 440, 129; 530/502

[56] References Cited

U.S. PATENT DOCUMENTS

| | | | |
|---|---|---|---|
| 4,339,534 | 7/1982 | Johansen et al. | 435/68.1 |
| 4,806,473 | 2/1989 | Johansen et al. | 435/71.1 |
| 5,185,258 | 2/1993 | Caldwell et al. | 435/220 |

FOREIGN PATENT DOCUMENTS

| | | |
|---|---|---|
| 0 085 516 | 8/1983 | European Pat. Off. . |
| 63233788 | 9/1988 | Japan . |
| 80/02157 | 10/1980 | WIPO . |
| 92/02615 | 2/1992 | WIPO . |
| WO 95/20039 | 7/1995 | WIPO . |

OTHER PUBLICATIONS

Sorensen, S.B. et al. *J. Am. Chem. Soc.* 117:5944–5950, (1995).

Bech et al., "Chemical Modifications of a Cysteinyl Residue Introduced in the Binding Site of Carboxypeptidase Y By Site–Directed Mutagenesis", *Carlsberg Res. Commun.*, 53:381 (1988).

Blachly–Dyson et al., "Yeast Carboxypeptidase Y Can be Translocated and Glycosylated Without its Amino–Terminal Signal Sequence", *J. Cell. Biol.*, 104:1183–1191 (1987).

Bongers, J., et al. "Comparison of Enzymatic Semisynthesis of Peptide Amides: Human Growth Hormone Releasing Factor and Analogs," *BioMed. Biochim. ACTA*, 50(10/11):157–162 (1991).

Bongers et al., "Semisynthesis of Human Growth Hormone–Releasing Factor by Trypsin Catalyzed Coupling of Leucine Amide to a C–Terminal Acid Precursor", *Int. J. Peptide Protein Res.*, 40:268–273 (1992).

Breddam et al., "Semisynthesis of Human Insulin Utilizing Chemically Modified Carboxypeptidase Y" *Carlsberg Res. Commun.*, 49:463–472 (1984).

Breddam et al., "Chemically Modified Carboxypeptidase Y with Increased Amidase Activity", *Carlsberg Res. Commun.*, 49:535–554 (1984).

Breddam et al., "Determination of C–Terminal Sequences by Digestion with Serine Carboxypeptidases: The Influence of Enzyme Specificity", *Carlsberg Res. Commun.*, 52:55–63 (1987).

Breddam et al., "Amidatioin of Growth Hormone Releasing Factor (I–29) by Serine CArboxypeptidase Catalyzed Transpeptidation", *Int. J. Peptide Res.*, 37:153–160 (1990).

Dal Degan et al., "Purification and Characterization of Two Serine Carboxypeptidase from *Aspergillus niger* and Their Use in C–terminal Sequencing of Proteins and Peptide Synthesis", *Appl. Environ. Microbiol.*, 58:2144–2152 (1992).

Endrizzi et al., "2.8Å Structure of Yeast Serine Carboxypeptidase", *Biochemistry*, 33:11106–11120 (1994).

Hayashi, "Carboxypeptidase Y", *Methods Enzymol.*, 45:568–587 (1976).

Henricksen et al., "Peptide Amidation by Chemical Protein Engineering: A Combination of Enzymatic and Photochemical Synthesis", *J. Am. Chem. Soc.*, 114:1876–1877 (1992).

Johansen, J. et al., "Isolation of Carboxypeptidase Y by Affinity Chromatography", *Carlsberg Res. Commun.*, 41(1):1–14 (1976).

Mortensen et al., "Site–Directed Mutagenesis on (Serine) Carboxypeptidase Y", *Biochemistry*, 33:508–517 (1994).

Mortensen, U. et al., "Recognition of C–terminal Amide Groups by (Serine) Carboxypeptidase Y Investigated by Site–directed Mutagenesis", *Journal of Biological Chemistry*, 269(22):15528–15532 (Jun. 3, 1994).

Mortensen, U. et al., "A Conserved Glutamic Acid Bridge in Serine Carboxypeptidases, Belonging to the $\alpha/\beta$ Hydrolase Fold, Acts as a pH–dependent Protein–stabilizing Element", *Protein Science*, 3:838–842 (1994).

Mortensen, U. et al., "Mechanistic Study on Carboxypeptidase Y–Catalyzed Transacylation Reactions. Mutationally Altered Enzymes for Peptide Synthesis", *J. Am. Chem. Soc.*, 116(1):34–41 (1994).

Nielsen et al., "Regulated Overproduction and Secretion of Yeast Carboxypeptidase Y", *Appl. Microbiol. Biotech.*, 33:307–312 91990).

Olesen et al., "Altering Substrate Preference or Carboxypeptidase Y by a Novel Strategy of Mutagenesis Eliminating Wild Type Background", *Protein Engineering*, 6:409–415 (1993).

Olesen, K. et al., "The Activity of Carboxypeptidase y Toward Substrates with Basic $P_1$ Amino Acid Residues is Drastically Increased by Mutational Replacement of Leucine 178," *Biochemistry*, 33:11121–11126 91994).

(List continued on next page.)

*Primary Examiner*—Robert A. Wax
*Attorney, Agent, or Firm*—Foley & Lardner

[57] ABSTRACT

A method for transamidating a peptide substrate having a $P_1$ amino acid residue with a positively charged side chain. According to the invention, carboxypeptidase Y is modified to substitute at least one amino acid having a negatively charged side chain in an $S_1$ subsite. Additionally, the modified carboxypeptidase Y can include substituted amino acid residues in an $S_1'$, $S_2$ and/or $S_3$ subsite to accommodate a specific peptide substrate.

28 Claims, No Drawings

OTHER PUBLICATIONS

Olesen, K. et al., "Extended Subsite Characterization of Carboxypeptidase Y Using Substrates Based on Intramolecularly Quenched Fluorescence", *Protein and Peptide Letters,* 3(2):67–74 (1996).

Raaschou–Nielsen, M. et al., "Improvement of the Applicability of Carboxypeptidase Y in Peptide Synthesis by Protein Engineering", *Peptide Research,* 7(3):132–135 (1994).

Robinson et al., "Protein Sorting in *Saccharomyces cerevisiae:* Isolation of Mutants Defective in the Delivery and Processing of Multiple Vacuolar Hydrolases", *Mol. Cell. Biol,* 8:4936(1988).

Rothman et al., "Protein Sorting in Yeast: Mutant Defective in Vacuole Biogenesis Mislocalize Vacuolar Proteins into the Late Secretory Pathway", *Cell,* 47:1041–1051 (1986).

Sakina et al., "Thermolysin–Catalyzed Synthesis of Peptide Amides", *Chem. Pharm. Bull.,* 36:4345–4354 (1988).

Sakina et al., "Protease–Catalyzed Semisynthesis of Human Neuropeptide Y", *Chem. Pharm. Bull.,* 37:811–812 91989).

Sherman, "Getting Started with Yeast", *Methods Enzymol.,* 194:3–21 (1991).

Siezen et al., "Engineering of the Substrate–Binding Region of the Subtilisin–Like Cell–Envelope Proteinase of Lactoccus Lactis," *Protein Engineering,* 6(8):927–937 (1993).

Sorensen et al., "Primary Structure of Carboxypeptidase II from Malted Barley", *Carlsberg Res. Commun.,* 52:285 (1987).

Sørensen, S. et al., "Site–Directed Mutagenesis on (Serine) Carboxypeptidase Y from Yeast. The Significance of Thr60 and Met398 in Hydrolysis and Aminolysis Reactions", *J. Am. Chem. Soc.,* 117(22):5944–5950 (1995).

Stennicke, H. et al., "Effects of Introduced Aspartic and Glutamic Acid Residues on the $P_I$ Substrate Specificity, pH Dependence and Stability of Carboxypeptidase Y", *Protein Engineering,* 7(7):911–916 (1994).

Stennicke, H. et al., "Evaluation of the Significance of Charge and Length of Side Chain on the $P_I$–$S_I$ Interactions in (Serine) Carboxypeptidase Y", *Protein and Peptide Letters,* 3(2):75–80 (1996).

Stennicke, H. et al., "Studies on the Hydrolytic Properties of (Serine) Carboxypeptidase Y", *Biochemistry,* 35(22):7131–7141 (1996).

Stevens et al., "Gene Dosage–dependent Secretion of Yeast Vacuolar Carboxypeptidase Y", *J. Cell Biol.,* 102:1551–1557 (1986).

Stevens et al., "Translocation, Sorting and Transport of Yeast Vacuolar Glycoproteins", *Yeast Cell biology,* Editor: J. Hicks, New York, Alan R. Liss, at pp. 519–536 (1986).

Tullin et al., "A High–Affinity Uptake System for Branched–Chain Amino Acids in *Saccharomyces cerevisiae",* *Yeast,* 7:933–941 (1991).

Valls et al., "Protein Sorting in Yeast: The Localization Determinant of Yeast Vacuolar Carboxypeptidase Y Resides in the Propeptide", *Cell,* 48:887–889 (1987).

Winther et al., "Increased Hydrophobicity of the S1' Binding Site in Carboxypeptidase Y Obtained by Site–Directed Mutagenesis," *Carlsberg Res. Commun.,* 50:273–284 (1985).

Winther et al., "Yeast Carboxypeptidase Y Requires Glycosylation for Efficient Intracellular Trnsport, But Not for Vacuolar Sorting, in vivo Stability, or Activity", *Eur: J. Biochem.,* 179:681 (1991).

```
                          SEQUENCE LISTING

<160> NUMBER OF SEQ ID NOS: 4

<210> SEQ ID NO 1
<211> LENGTH: 44
<212> TYPE: PRT
<213> ORGANISM: Homo sapiens
<220> FEATURE:
<221> NAME/KEY: VARIANT
<222> LOCATION: (44)
<223> OTHER INFORMATION: C-terminal amino acid which serves as a leaving
      group, typically, an uncharged amino acid side
      chain, preferably alanine

<400> SEQUENCE: 1

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Xaa
        35                  40

<210> SEQ ID NO 2
<211> LENGTH: 37
<212> TYPE: PRT
<213> ORGANISM: Homo sapiens
<220> FEATURE:
<221> NAME/KEY: VARIANT
<222> LOCATION: (37)
<223> OTHER INFORMATION: C-terminal amino acid which serves as a leaving
      group, typically, an uncharged amino acid side
      chain, preferably alanine

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Xaa
        35

<210> SEQ ID NO 3
<211> LENGTH: 31
<212> TYPE: PRT
<213> ORGANISM: Homo sapiens
<220> FEATURE:
<221> NAME/KEY: VARIANT
<222> LOCATION: (31)
<223> OTHER INFORMATION: C-terminal amino acid which serves as a leaving
      group, typically, an uncharged amino acid side
      chain, preferably alanine

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
            20                  25                  30

<210> SEQ ID NO 4
<211> LENGTH: 421
```

<212> TYPE: PRT
<213> ORGANISM: Saccharomyces cerevisiae

<400> SEQUENCE: 4

```
Lys Ile Lys Asp Pro Lys Ile Leu Gly Ile Asp Pro Asn Val Thr Gln
  1               5                  10                  15

Tyr Thr Gly Tyr Leu Asp Val Glu Asp Glu Asp Lys His Phe Phe Phe
             20                  25                  30

Trp Thr Phe Glu Ser Arg Asn Asp Pro Ala Lys Asp Pro Val Ile Leu
         35                  40                  45

Trp Leu Asn Gly Gly Pro Gly Cys Ser Ser Leu Thr Gly Leu Phe Phe
     50                  55                  60

Glu Leu Gly Pro Ser Ser Ile Gly Pro Asp Leu Lys Pro Ile Gly Asn
 65                  70                  75                  80

Pro Tyr Ser Trp Asn Ser Asn Ala Thr Val Ile Phe Leu Asp Gln Pro
                 85                  90                  95

Val Asn Val Gly Phe Ser Tyr Ser Gly Ser Ser Gly Val Ser Asn Thr
            100                 105                 110

Val Ala Ala Gly Lys Asp Val Tyr Asn Phe Leu Glu Leu Phe Phe Asp
        115                 120                 125

Gln Phe Pro Glu Tyr Val Asn Lys Gly Gln Asp Phe His Ile Ala Gly
130                 135                 140

Glu Ser Tyr Ala Gly His Tyr Ile Pro Val Phe Ala Ser Glu Ile Leu
145                 150                 155                 160

Ser His Lys Asp Arg Asn Phe Asn Leu Thr Ser Val Leu Ile Gly Asn
                165                 170                 175

Gly Leu Thr Asp Pro Leu Thr Gln Tyr Asn Tyr Tyr Glu Pro Met Ala
            180                 185                 190

Cys Gly Glu Gly Gly Glu Pro Ser Val Leu Pro Ser Glu Glu Cys Ser
        195                 200                 205

Ala Met Glu Asp Ser Leu Glu Arg Cys Leu Gly Leu Ile Glu Ser Ser
    210                 215                 220

Tyr Asp Ser Gln Ser Val Trp Ser Cys Val Pro Ala Thr Ile Tyr Cys
225                 230                 235                 240

Asn Asn Ala Gln Leu Ala Pro Tyr Gln Arg Thr Gly Arg Asn Val Tyr
                245                 250                 255

Asp Ile Arg Lys Asp Cys Glu Gly Gly Asn Leu Cys Tyr Pro Thr Leu
            260                 265                 270

Gln Asp Ile Asp Asp Tyr Leu Asn Gln Asp Tyr Val Lys Glu Ala Val
        275                 280                 285

Gly Ala Glu Val Asp His Tyr Glu Ser Cys Asn Phe Asp Ile Asn Arg
    290                 295                 300

Asn Phe Leu Phe Ala Gly Asp Trp Met Lys Pro Tyr His Thr Ala Val
305                 310                 315                 320

Thr Asp Leu Leu Asn Gln Asp Leu Pro Ile Leu Val Tyr Ala Gly Asp
                325                 330                 335

Lys Asp Phe Ile Cys Asn Trp Leu Gly Asn Lys Ala Trp Thr Asp Val
            340                 345                 350

Leu Pro Trp Lys Tyr Asp Glu Glu Phe Ala Ser Gln Lys Val Arg Asn
        355                 360                 365

Trp Thr Ala Ser Ile Thr Asp Glu Val Ala Gly Glu Val Lys Ser Tyr
    370                 375                 380

Lys His Phe Thr Tyr Leu Arg Val Phe Asn Gly Gly His Met Val Pro
385                 390                 395                 400
```

```
Phe Asp Val Pro Glu Asn Ala Leu Ser Met Val Asn Glu Trp Ile His
            405                 410                 415
Gly Gly Phe Ser Leu
            420
```

MODIFIED CARBOXYPEPTIDASE

BACKGROUND OF THE INVENTION

A preferred method for the production of peptides, particularly for pharmaceutical use, is through genetic engineering. However, the production of peptides by recombinant technologies has specific limitations. For example, because the genetic code does not include non-naturally occurring L-amino acids, D-amino acids, radioactive amino acids, and other detectable labels, production of recombinant peptides bearing such modifications is difficult.

In addition, natural amino acid modifications such as C-terminal amide group substitution, performed routinely in vivo, are difficult to perform in vitro. Because these post-translational modifications often result in the most potent or longest acting form of the peptide, they are the form most needed and desired for pharmaceutical use. For many peptides, C-terminal amidation is important for biological activity. However, recombinant expression systems for large scale production of active peptides cannot easily carry out the necessary C-terminal modification.

Carboxypeptidase enzymes are known to catalyze transpeptidation reactions, yielding C-terminally amidated peptides. However, wild type carboxypeptidase enzymes are not useful for C-terminal amidation of many peptides. For example, the inherent substrate specificity of wild-type carboxypeptidase restricts the variety of peptides that may be modified using this enzyme.

In particular, carboxypeptidase Y displays a strong preference for peptides with a penultimate apolar residue. Substrates having a penultimate amino acid with a positively charged side chain are not effectively transacylated by carboxypeptidase Y. For example, the substrate FA-Arg-Ala-OH is hydrolyzed about 500 times more slowly than the substrate FA-Leu-Ala-OH. Unfortunately, the amino acid sequences of many pharmaceutically important peptides, including growth hormone releasing factor (GRF) or glucagon like peptide (GLP1), have a penultimate or ultimate amino acid with a positively charged side chain, making transamidation with carboxypeptidase Y commercially impractical.

Although several mutant carboxypeptidases are known to have enhanced hydrolysis activity with a variety of peptide substrates, the study of numerous mutant carboxypeptidase enzymes demonstrates that there is no specific correlation between mutants having enhanced hydrolysis activity and mutants having enhanced transamidation activity. For example, although the carboxypeptidase S1 from *Penicillium janthinellum* is capable of efficiently hydrolyzing peptide substrates with a basic $P_1$ residue, the enzyme does not efficiently transpeptidate them. Breddam, *Carlsberg Res. Commun.*, 53(5):309–320 (1988).

It would be very useful to provide a modified carboxypeptidase having improved activity for transacylation of peptide substrates whose sequence includes a penultimate amino acid ($P_1$) having a positively charged side chain.

SUMMARY OF THE INVENTION

A modified carboxypeptidase and method of transamidation is provided in the instant invention. The modified carboxypeptidase and method effectively improve the activity of carboxypeptidase Y for transacylation of peptide substrates whose sequence includes a penultimate amino acid ($P_1$) having a positively charged side chain.

The modified carboxypeptidase of the invention includes at least one amino acid substitution in its $S_1$ subsite, which results in a more negative charge in the $S_1$ subsite as compared with the native carboxypeptidase. Typically, this is accomplished by substitution of an amino acid residue having a neutral or positively charged side chain with an amino acid residue having a negatively charged side chain. Examples of preferred positions within the $S_1$ subsite for the introduction of negative charge include positions L178, W312, N241 and L245. Examples of amino acids having negatively charged amino acid side chains include aspartic acid and glutamic acid. The modified carboxypeptidase Y can also include other mutations, such as substitutions at amino acid residues in one or more of the carboxypeptidase $S_1'$, $S_2$, and $S_3$ subsites. These additional modifications can further enhance transamidation of a particular substrate, and serve to accommodate the substrate and nucleophile for the transamidation reaction.

The method of the invention includes reacting the peptide substrate with a nucleophile in the presence of the modified carboxypeptidase Y. Examples of suitable nucleophiles include alkyl amines, benzyl amines and the α-amino group of amino acids. The amino acid nucleophiles may have an α-carboxylate group in the form of an acid, an ester or an amide. Preferably, the peptide substrate is incubated with the nucleophile and modified carboxypeptidase Y at a pH of about 6.3 to about 6.7.

A further aspect of the invention includes a modified carboxypeptidase Y having at least one of amino acid residues N241 or L245 substituted with an amino acid having a negatively charged side chain. The modified carboxypeptidase Y preferably also includes additional substitutions within the $S_1$ subsite, most preferably at positions L178 and/or W312. The modified carboxypeptidase Y can further include amino acid substitutions at amino acid residues in one or more of the carboxypeptidase subsites $S_1'$, $S_2$ and $S_3$.

The modified carboxypeptidase of the invention is especially useful for post-translational modification of recombinant peptides, specifically, peptides having a penultimate amino acid residue with a positively charged side chain. However, it is understood that peptides produced by means other than recombinant technology can be transamidated according to the method of the invention.

DETAILED DESCRIPTION OF THE INVENTION

The modified carboxypeptidase of the invention is designed to improve or enhance transamidation of a peptide substrate having a positively charged penultimate amino acid residue. Preferably the modified carboxypeptidase is derived from a known serine or cysteine carboxypeptidase, such as carboxypeptidase Y.

To facilitate an understanding of the invention, a brief discussion of the terminology used in connection with the invention will first be provided.

Terminology

The present disclosure uses the terminology of Schechter et al., 1967, *Biochem. Biophys. Res. Commun.* 27:157–162, to describe the location of various amino acid residues on the peptide substrate and within the active site of the carboxypeptidase enzyme.

According to the terminology of Schechter et al., the amino acid residues of the peptide substrate are designated by the letter "P". The amino acids of the substrate on the N-terminal side of the peptide bond to be cleaved (the "cleavage site") are designated $P_n \ldots P_3$, $P_2$, $P_1$ with $P_n$ being the amino acid residue furthest from the cleavage site.

Amino acid residues of the peptide substrate on the C-terminal side of cleavage site are designated $P_1'$, $P_2'$, $P_3'$ . . . $P_n'$ with $P_n'$ being the amino acid residue furthest from the cleavage site. Hence, the bond which is to be cleaved (the "cleavage site") is the $P_1$—$P_1'$ bond. Since a carboxypeptidase only cleaves the peptide bond between the C-terminal and penultimate residue, substrates for carboxypeptidase enzymes only include a residue in a $P_1'$ position on the C-terminal side (i.e., there are no $P_2'$, $P_3'$, etc. residues). The generic formula for the amino acids of the substrate of the carboxypeptidase is as follows:

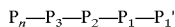

$$P_n\text{—}P_3\text{—}P_2\text{—}P_1\text{—}P_1'$$

The "active site" of a carboxypeptidase enzyme can be divided into multiple substrate binding subsites. The designation of the substrate binding sites of a carboxypeptidase is analogous to the designation of amino acid residues of the peptide substrate. However, the binding subsites of the carboxypeptidase are designated by the letter "S" and can include more than one amino acid residue. The substrate binding sites for the amino acids on the N-terminal site of the cleavage site are labeled $S_n$ . . . $S_3$, $S_2$, $S_1$. The substrate binding subsite for the amino acid on the carboxy side of the cleavage site is designated $S_1'$. Hence, in a carboxypeptidase, the $S_1'$ subsite interacts with the "leaving group" of the peptide substrate and the incoming nucleophile. A generic formula for describing substrate binding sites of a carboxypeptidase is:

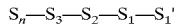

$$S_n\text{—}S_3\text{—}S_2\text{—}S_1\text{—}S_1'$$

The $S_1$ binding site binds the side chain of the penultimate amino acid, $P_1$, of the peptide substrate. The $S_2$ binding site interacts with the side chain of the neighboring amino acid residue, $P_2$. Likewise, the $S_3$ binding site interacts with the side chain of the $P_3$ residue.

As used herein, a nucleophile is a molecule that donates a pair of electrons to an electron acceptor, in this case the α-carboxylate group acyl carbon of the peptide substrate penultimate amino acid residue, to form a covalent bond. Suitable nucleophiles include amino acids; amino acid derivatives, such as amino acid esters and amino acid amides; amides, such as ammonia; or benzyl amines. One specific group of compounds suitable for use in the present method include nucleophiles that are cleavable (in a step subsequent to the transamidation reaction) to produce a peptide lacking the residue derived from the nucleophile and having a C-terminal carboxamide. Examples include a nucleophiles that are cleavable by photolysis, solvalysis, reduction, rearrangement, hydrolysis or oxidation, such as those disclosed in U.S. Pat. No. 5,580,751, incorporated herein by reference. It should be noted that the penultimate residue of the substrate peptide becomes the ultimate residue after the C-terminal residue has been cleaved off the transamidation product.

The invention includes a "modified carboxypeptidase" derived from a known serine or cysteine carboxypeptidase, wherein certain amino acid residues have been substituted with a different amino acid to provide a carboxypeptidase capable of improved transamidation. "Improved transamidation" can be monitored by measuring the fraction of aminolysis obtained (fa).

$$fa = \frac{\text{aminolysis products}}{\text{hydrolysis} + \text{aminolysis products}}$$

Because a low fraction of aminolysis may be due to degradation of the transamidation product by hydrolysis, it is preferred that the modified carboxypeptidase have a fraction of aminolysis (fa) at least about 0.1 greater when compared to the corresponding native carboxypeptidase.

Another useful measurement of enzyme efficiency is $K_{N(app)}$, the concentration at which $fa_{max}/2$ is reached. $K_{N(app)}$ describes the apparent binding constant of the nucleophile. Because the competing hydrolysis reaction predominantly occurs while the leaving group is still bound to the enzyme, a low $K_{N(app)}$ is preferable.

Transamidation

The modified carboxypeptidase of the invention is capable of improved transamidation of a peptide substrate having a positively charged amino acid residue in a $P_1$ subsite, when compared to the corresponding native carboxypeptidase. As used herein, "transacylation" is a reaction in which a leaving group is exchanged for a nucleophile. Transacylation reactions include transamidation and transpeptidation reactions. "Transpeptidation", as used herein, occurs when an amino acid or amino acid derivative acts as the leaving group and the nucleophile is an amino acid, or amino acid derivative, such as an amino acid ester or amino acid amide. "Transamidation" includes transpeptidation, in that an amide bond is formed between the nucleophile and the peptide substrate. However, in a transamidation reaction, the nucleophile is not necessarily an amino acid.

A general transacylation reaction is shown below:

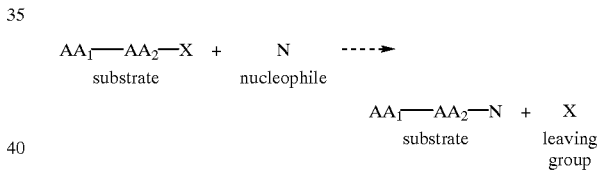

According to the invention, a peptide substrate is allowed to react with a nucleophile in the presence of a modified carboxypeptidase to form a product in which the nucleophile is connected, by an amide bond, to an α-carboxylic group of the $P_1$ residue of the peptide substrate. C-terminal amidation of a peptide by a serine carboxypeptidase is a two step reaction. In the first step, the enzyme attacks the C-terminal peptide bond, displacing the $P_1'$ "leaving group" and forming an acyl bond between the $P_1$ residue of the peptide substrate and the enzyme. This intermediate is referred to as an "acyl-enzyme intermediate". In the presence of an appropriate nucleophile, under proper conditions, the enzyme causes the nucleophile to add to the cleaved peptide substrate to produce an amidated transpeptidation product. It is believed that the nucleophile attaches to the carboxyl group of the acyl-enzyme intermediate and displaces the enzyme from the acyl-enzyme intermediate. In this manner, the nucleophile becomes linked to the carboxyl group of the peptide substrate. Alternatively, the acyl-enzyme intermediate may be deacylated by water to produce a hydrolysis product. The modified carboxypeptidase of the invention is designed to preferentially produce the amidated transpeptidation product over the hydrolysis product.

Scheme I, shown below, is a schematic representation of a carboxypeptidase catalyzed transamidation reaction in which E represents the free enzyme; S, the substrate; ES, the enzyme substrate complex; EAP, the acyl-enzyme intermediate with the leaving group bound where A is the acyl-component and P is the leaving group; EA is the acyl enzyme; N, the nucleophile; and AN, the desired aminolysis product.

Scheme I

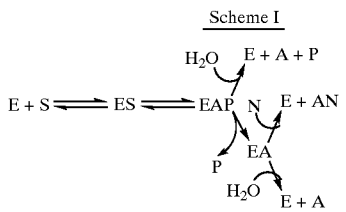

As illustrated in scheme I, hydrolysis can occur at two stages during transamidation. The acyl-enzyme intermediate can be hydrolyzed to release the acyl-component and the leaving group from the enzyme, without the production of the desired aminolysis product. It is presently believed that hydrolysis predominantly occurs at this point during the transamidation reaction. Alternatively, the acyl-enzyme may be hydrolyzed after the leaving group has withdrawn from the acyl-enzyme intermediate.

Modified Carboxypeptidase

The modified carboxypeptidase of the invention is designed to improve or enhance transamidation of a peptide substrate when compared to a native serine or cysteine carboxypeptidase. The basis for the modifications to the native carboxypeptidase is to provide the "best fit" between the peptide substrate and the active site of the enzyme. Factors considered when making a modification include reduction in steric hindrance and reduction in water access to the acyl-enzyme intermediate.

In particular, the modified carboxypeptidase is designed to improve or enhance transamidation of a peptide substrate having a positively charged penultimate amino acid residue by substituting an amino acid residue of the $S_1$ subsite with an amino acid having a negatively charged side chain. To enhance transamidation of a peptide substrate having a positively charged amino acid at position $P_3$, in addition to a positively charged residue at $P_1$, a secondary substitution can be made where a residue in the $S_3$ subsite, or in another subsite position capable of interacting with a peptide substrate $P_3$ residue, is substituted with an amino acid residue having a negatively charged side chain. For a peptide substrate having an alanine residue at position $P_2$, a residue in an $S_2$ subsite of the carboxypeptidase may be substituted with an amino acid residue having a hydrophobic side chain. In particular, the modified carboxypeptidase can be used to improve transamidation of a growth hormone releasing factor (GRF) precursor or a glucagon like peptide (GLP) precursor. The sequences for GRF(1-44), GLP1(1-36)-Xaa, and GLP(7-36)-Xaa are shown below, where Xaa is the C-terminal amino acid residue which serves as the leaving group. The Xaa residue typically has an uncharged amino acid side chain and preferably is an alanine residue.

Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Xaa    GRF (1-43)-Xaa [SEQ ID NO:1]

His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Xaa    GLP 1 (1-36)-Xaa [SEQ ID NO:2]

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Xaa    GLP 1 (7-36)-Xaa [SEQ ID NO:3]

To produce the modified carboxypeptidase of the invention, site specific mutagenesis can be performed to substitute amino acid residues within the active site of a native carboxypeptidase. Specifically, site specific mutagenesis can be performed to substitute amino acid residues in an $S_1$ subsite with negatively charged amino acid residues. To further enhance the transamidation activity of the modified carboxypeptidase, additional substitutions are made to amino acid residues within an $S_2$, $S_3$ or $S_1'$ subsite. Additionally, the transamidation reaction is preferably carried out at a pH of about 6.3 to about 6.7 to further enhance the efficiency of the reaction.

Substitutions in the $S_1$ subsite

The $S_1$ subsite of a carboxypeptidase enzyme interacts with a penultimate C-terminal residue of the peptide substrate. Frequently, the $S_1$ subsite plays an important role in determining the substrate specificity of the carboxypeptidase. This is particularly true for carboxypeptidase Y.

A first aspect of the invention is directed to a method for transamidating a peptide substrate having a positively charge penultimate amino acid residue. According to the invention, an amino acid having a negatively charged side chain is introduced in an $S_1$ subsite of the carboxypeptidase to produce a carboxypeptidase with enhanced transamidation activity with a peptide substrate having a positively charged $P_1$ residue.

When used in the context of the invention, the phrase "an amino acid having a negatively charged side chain" includes L-amino acids, and amino acid derivatives such as amino acid esters or amino acid amides. Examples of suitable amino acids having negatively charged side chains include aspartic acid and glutamic acid.

In one embodiment, an amino acid having a negatively charged side chain is introduced in at least one of positions N241, L245, L178, or W312 within an $S_1$ subsite of carboxypeptidase Y. Examples of preferred substitutions include N241D, N241E, L245D, L245E, L178D, L178E, W312D and W312E.

Additional substitutions within the $S_1$ subsite for enhancing transamidation include L178A, L 178S, and W312L. Substituting alanine or serine for leucine at position 178, or leucine for tryptophan at position 312, results in the replacement of the original amino acid residue with either a less bulky residue or a more polar residue. It is believed that the introduction of a less bulky residue enhances transamidation by reducing steric hindrance. The size of the $S_1$ binding site is thereby enlarged to improve transamidation of a peptide having a $P_1$ amino acid residue with a relatively long side chain, such as arginine or lysine. A polar residue, such as serine, can also provide a more favorable environment for a charged $P_1$ residue.

Substitutions in the $S_1'$ subsite

Transamidation of a specific peptide substrate by the modified carboxypeptidase of the invention can be further enhanced by substitution of an amino acid residue in an $S_1'$ subsite of a native carboxypeptidase. In a transamidation reaction, the $S_1'$ subsite interacts with the incoming nucleophile and the leaving group of the peptide substrate. Because the competing hydrolysis reaction is thought to predominantly occur while the leaving group is still bound to the enzyme, a substitution in the $S_1'$ subsite that increases the rate of dissociation of the leaving group from the acyl-enzyme intermediate and/or decreases water access while the leaving group is still bound, would increase the fraction of aminolysis obtained by decreasing the competing hydrolysis reaction. Preferably, the substitution does not adversely affect binding of the nucleophile to the peptide substrate.

Positions within the $S_1'$ subsite where an effective substitution may be made include T60, F64, L267, L272, S297 and M398. These residues define the $S_1'$ side chain binding pocket of carboxypeptidase Y. Other suitable residues for substitution include Y49, N51, E65 and E145. These residues form a hydrogen bond network within the $S_1'$ subsite. The following mutant carboxypeptidases displayed an improvement in fraction of aminolysis obtained, for a larger, hydrophobic leaving group, such as a leucine residue, when compared to a wildtype carboxypeptidase: T60A, T60W, T60Y, T60D, M398G, M398A, M398V, M398I, M398L, M398F, M398Y, M398C, M398N, and M398E. The most dramatic improvement was observed with the following mutants: T60Y, M398V, M398I, M398L, M398F, M398Y, M398C, and M398E. Multiple substitutions, for example at both T60, M398, and/or N51 further enhanced the fraction of aminolysis obtained with the mutant enzyme.

Substitutions in the $S_2$ subsite

The activity of the modified carboxypeptidase may be further enhanced for a peptide substrate having a $P_2$ alanine residue using a carboxypeptidase having a substitution in the $S_2$ subsite. Because the $S_2$ subsite of the carboxypeptidase interacts with the substrate residue at $P_2$, introduction of a hydrophobic residue, such as phenylalanine or alanine in the $S_2$ subsite complements the peptide substrate and can enhance transamidation of the substrate with the carboxypeptidase. In particular, transamidation of a substrate having a $P_2$ alanine may be increased by mutant carboxypeptidases which include the following substitutions: E296F, S297A, N303A and N303F.

Substitutions in the $S_3$ subsite

In addition to introducing a negatively charged residue in an $S_1$ subsite, transamidation of a peptide substrate having positively charged residues at both $P_1$ and $P_3$ can be further enhanced by introducing a secondary substitution, such as a negatively charged residue in an $S_3$ subsite or other position capable of interacting with a peptide substrate $P_3$ residue. It is believed that the introduction of a second negatively charged residue can reduce competition between the two basic amino acid residues on the peptide substrate for a negatively charged residue in the $S_1$ subsite.

Preferably, a negatively charged amino acid residue is introduced in an $S_3$ subsite, or in a position capable of interacting with a peptide substrate $P_3$ residue, for example, at position N241, N242, L245 or A246. Examples of suitable substitutions include N241D, N241E, N242D, N242E, L245D, L245E, A246D and A246E. Positions N241 and L245 appear to interact with both $P_3$ and $P_1$ residues on a substrate peptide.

Other Modifications to enhance transacylation

Although carboxypeptidase Y is capable of transamidating peptide substrates over a broad pH range (from about pH 4 to about pH 10), the pH at which a transamidation reaction is performed can affect the substrate or product preference of a carboxypeptidase enzyme. To improve transamidation yields, the pH should be such that the enzyme favors the peptide substrate over the product. The optimal pH of a transamidation reaction will vary depending on the peptide substrate, nucleophile and desired product. Typically, a transamidation reaction is optimally performed at a pH between about 5.5 and about 8.5. It was found that transamidation of a peptide substrate using a modified carboxypeptidase enzyme having a substitution at positions L178 and M398 (L178S+M398L) is preferably performed at a pH of about 6.3 to about 6.7.

Additionally, the fraction of aminolysis obtained can be increased by increasing the concentration of available nucleophile.

Site directed mutagenesis

According to the method of the invention, mutation of a known serine or cysteine carboxypeptidase can be accomplished through site specific mutagenesis. Site specific mutagenesis requires knowledge of the DNA sequence of the carboxypeptidase and the location of codons which code for the substrate binding site amino acids. The DNA sequence and restriction map of the PRC1 gene which encodes carboxypeptidase Y and a source of the DNA sequence is described in Valls et al., *Cell*, 48:887–889 (1987).

Amino acids in the active site, such as those in the $S_1$, $S_1'$, $S_2$ and $S_3$ subsites, can be modified by altering a codon that encodes an amino acid in the DNA sequence of a known carboxypeptidase. According to the invention, the modified DNA sequence includes a codon or codons encoding amino acids within the active site of the carboxypeptidase. Preferably, modification of the carboxypeptidase involves substitution of a codon encoding a different amino acid than that encoded by a codon in the active site of a known serine or cysteine carboxypeptidase. Preferably, the substitution involves a codon which encodes an amino acid in the $S_1$, $S_1'$, $S_2$ or $S_3$ binding subsites of the carboxypeptidase. Codons for amino acids are known to those of skill in the art.

Site specific mutagenesis can be accomplished through incorporation of an oligonucleotide containing a mutated or modified codon at the chosen codon location. Other methods of site specific mutagenesis can be employed as described by Maniatis et al., *A Guide to Molecular Cloning* (1989). Preferred methods for incorporation of the oligonucleotide into the DNA sequence encoding a known carboxypeptidase include polymerase chain reaction (PCR) and standard cloning technology.

Oligonucleotides containing a modified codon can be obtained by standard methods including automated synthesis. Methods for automated DNA synthesis are known to those of skill in the art.

Once formed, the synthetic oligonucleotide is incorporated into the DNA sequence of a known carboxypeptidase in frame. Insertion of the synthetic oligonucleotide can be accomplished by cleavage with at least one restriction endonuclease such that that the DNA sequence within the targeted site is deleted, followed by ligation of the synthetic oligonucleotide into the site from which the original DNA sequence was deleted. An appropriate restriction endonuclease can be determined by examining the nucleotide sequence around the targeted site and by the size of the synthetic oligonucleotide to be inserted at the site. The recognition sequences of restriction enzymes are known to those of skill in the art, and an appropriate combination of enzymes can be readily selected by one of skill in the art.

Expression of a modified carboxypeptidase

In a preferred version, the codon for an amino acid in the $S_1$ subsite of carboxypeptidase Y is modified to encode an amino acid having a negatively charged side chain, e.g., glutamic acid or aspartic acid. To effect the substitution of amino acids in the carboxypeptidase, the gene encoding the carboxypeptidase is mutated to express the desired substituted amino acid, using known methods of site-directed mutagenesis.

The PRC1 gene encoding carboxypeptidase Y can be obtained from plasmid pTSY3, available from the American Type Culture Collection (ATCC) in Manassas, Va., under Accession No. 75580. An oligonucleotide including the desired substituted sequence, that is, containing a codon for the amino acid substitution at a site corresponding to the native codon is synthesized, for example, by automated DNA synthesis. PCR techniques can be used to incorporate the substitution into the carboxypeptidase Y gene.

The modified DNA sequence is then incorporated into a vector to provide for selection and expression. Suitable vectors include yeast bacterial shuttle vectors YEp24, pRA21ΔBAM, pYSP1, pTSY3, pRA21, and pYSP32. The modified DNA sequence is incorporated into the vectors by known, standard methods as described by Maniatis et al., cited supra, and Nielsen et al., *Appl. Microbiol. Biotechnol.*, 33:307 (1990).

The vector is introduced into a suitable host cell for selection and expression. Suitable host cells include bacteria, such as *E. coli*, and yeast, such as *S. cerevisiae*. Preferred host cells include *S. cerevisiae* strains having isogenic vp1 mutations, delta-prc1 mutations and ura3 mutations. Especially preferred hosts are *S. cerevisiae* strains that have vp1 mutations resulting in secretion of active carboxypeptidase Y, as described in Nielsen et al., cited supra. The preferred vector is a plasmid pTSY which is the yeast bacterial shuttle vector YEp24 with a 3.2 kb DNA insert containing the PRC1 gene under the control of the PRC1 promoter, described above.

Suitable host cells are transformed by standard methods including transformation with calcium phosphate, calcium chloride or lithium acetate competent cells, microinjection, and electroporation. Transformed cells are selected based upon the presence of antibiotic resistance in the case of *E. coli* or based upon the presence of URA3 in the case of yeast. Transformed yeast cells are screened for the production of mutant carboxypeptidase activity by detecting the ability of the transformed cells to hydrolyze a peptide substrate using standard methods as described by Nielsen et al., cited supra.

Once the transformed cells are selected and amplified, the modified carboxypeptidase can be purified using standard methods such as high performance liquid chromatograph and affinity chromatography.

Transamidation of substrates using the modified carboxypeptidase

The invention also provides a method for using the modified carboxypeptidase to transamidate a peptide substrate with a nucleophile. The modified carboxypeptidase of the invention is designed to improve transamidation of a peptide substrate having a positively charged penultimate amino acid residue.

Transamidation is generally performed in an aqueous buffer solution. Preferred buffer solutions include 50 mM HEPES and 5 mM EDTA, pH 7.5 or 50 mM CHES and 5 mM EDTA, pH 9.5. It is important that the chosen buffer is unable to act as a nucleophile in the transamidation reaction.

Production of the transamidation product is typically monitored by HPLC or another appropriate analytical technique. The reaction is stopped by addition of an acidic solution to reduce the pH of the reaction mixture to about pH 1 to 3. Alternatively, the reaction may be stopped by adding an enzyme inhibitor such as phenyl-methane sulfonyl fluoride (PMSF) or diisopropyl fluorophosphate (DFP). The transamidation product may be separated from the reaction mixture by reverse phase chromatography, hydrophobic interaction chromatography, ion exchange chromatography, or HPLC.

Alternatively, the transamidation reaction is performed in an organic solvent. Suitable organic solvents for transamidation include dimethyl sulfoxide (DMSO), N,N'-dimethylacetamide, dimethylformamdie and other similar solvents. The methodology for transamidation in organic solvents is described in Bongers et al., *Int. J Peptide Protein Res.*, 40:268 (1992).

In one example for transamidation in an aqueous solution, a peptide substrate, GRF(1-44)-Ala, is dissolved in a 5% solution of acetic acid. A nucleophile, such as a leucine amide, is dissolved in 50 mM HEPES, 5 mM EDTA to a final concentration of 500 mM. 25 μl of a 40 mM solution of GRF(1-44)-Ala is added per 950 μl of nucleophile solution and the pH is 7.5 at 20° C. A modified carboxypeptidase, such as L178S+M398L+N51Q modified carboxypeptidase Y, is added to the mixture in 25 μl of water per ml solution, resulting in an enzyme concentration of about 0.002 to 0.07 mg/ml. The reaction is monitored using HPLC and is stopped by the addition of one volume of 2.5% trifluoroacetic acid when no additional product is formed.

In another example, the peptide substrate, GLP1(7-36)-Ala, is dissolved in a 5% solution of acetic acid. The nucleophile, O-Nitrophenylglycinamide ("ONPGA"), is dissolved in 50 mM HEPES, 5 mM EDTA to a final concentration of 250 mM 25 μl of a 40 mM solution of GLP1 (7-36)-Ala is added per 950 μl of nucleophile solution and the pH is 7.5 at 20° C. A modified carboxypeptidase, such as L178S+M398L+N51Q modified carboxypeptidase Y, is added to the mixture in 25 μl of water per ml solution, resulting in an enzyme concentration of about 0.002 to 0.07 mg/ml. The reaction is followed by HPLC and is stopped when no additional product is formed by the addition of one volume of 2.5% trifluoroacetic acid.

The reaction product of the transpeptidation reaction, GLP1(7-36)-ONPGA, may be cleaved by photolysis. GLP1 (7-36)-ONPGA, in 12.5 ml methanol is added to 80 mM NaHSO$_3$ (12.5 ml) and pH is adjusted to 9.5 with 5N NaOH. The reaction mixture is then purged with N$_2$ for 15 minutes and subsequently photolyzed under a nitrogen atmosphere using a SP 200 lamp. The photolysis is then followed by extraction of samples for analysis at 0, 30, 60 and 120 minutes. Each sample is analyzed using HPLC and the results are compared with the control sample.

Any of the modifications to carboxypeptidase disclosed herein are suitable for use in either of the two transamidation reactions discussed above. The modified carboxypeptidase includes a substitution in which a negatively charged amino acid residue is introduced in an $S_1$ subsite, preferably, at position 178. A suitable substitution includes L178D or E. Preferably, the modified carboxypeptidase further includes a substitution at an $S_1'$ subsite, preferably at position M398. A suitable substitution includes M398L. Additionally, the modified carboxypeptidase can further include a substitution to introduce an amino acid residue having a negatively charged side chain capable of interacting with a positively charged amino acid residue in the peptide substrate $P_3$ position, for example, at positions 241 or 245. The carboxypeptidase used to transamidate the GRF precursor, preferably has a hydrophobic substitution at an $S_2$ subsite to enhance the interaction of the carboxypeptidase with the $P_2$ alanine residue.

EXAMPLES

The invention will be further characterized by the following examples. These examples are not meant to limit the scope of the invention which has been fully set forth in the foregoing description. Variation within the concepts of the invention are apparent to those skilled in the art.

Example 1

Methods:

The mutant carboxypeptidase enzymes used in these studies were produced by site-directed mutagenesis, essentially following the procedures described in published PCT Patent Application No. WO 95/20039. In general, oligonucleotides synthesized to encode the amino acid substitution were used to produce the mutant enzymes.

Transamidation reactions were carried out generally as described in PCT Application WO 95/20039. In general, the method included dissolving the nucleophile (H-Leu-NH$_2$, unless otherwise indicated) in 50 mM HEPES, 5 mM EDTA and adjusting the pH to 7.5. 5 μl of peptide substrate (8 mM Bz-G-A-R-A-R-A-OH, unless otherwise indicated, in methanol) was added to 190 μl nucleophile solution followed by 5 μl enzyme, resulting in a substrate concentration of 0.2 mM.

During the reaction, 20 μl aliquots were removed from the reaction mixture and added to 50 μl 1% trifluoroacetic acid to quench the reaction. The reactant composition was determined by HPLC using a Waters HPLC equipped with a C-18 Waters Novapac 4μ reverse phase column and various gradients of acetonitrile in 0.1% trifluoroacetic acid. The separation was monitored at 254 nm allowing the direct quantification of the products from the integrated peak areas. The composition of the reaction mixture was determined at least twice during the reaction, the first when 20–50% (preferably 35%) of the substrate had been consumed in the reaction and the second time when 50–90% (preferably 80%) of the peptide substrate had been consumed.

The reaction products were collected and identified by amino acid analysis after acid hydrolysis using a Pharmacia Alpha Plus analyzer. Further identification was obtained by co-chromatography of authentic standard compounds.

The fraction of aminolysis (fa) was expressed as the ratio between the formed aminolysis product and the sum of all products formed. Unconsumed substrate was disregarded in the calculations.

TABLE 1

Fraction of aminolysis (fa) for carboxypeptidase Y and $S_1$ mutants in transpeptidation of a substrate having an argninine at $P_1$

| Enzyme | t (min) | [N] (mM) | S (%) | P (%) | fa |
|---|---|---|---|---|---|
| Wild type | 29400 | 375 | 86 | 0.7 | 0.05 |
| L178A | 112 | 375 | 18 | 37 | 0.45 |
| L178S | 40 | 375 | 16 | 37 | 0.72 |
| L178D | 130 | 375 | 23 | 62 | 0.81 |
| N241E | 78 | 50 | 50 | 13 | 0.27 |
| L245E | 110 | 50 | 50 | 3.5 | 0.07 |
| L245E | 1100 | 375 | 50 | 10 | 0.18 |
| W312L | 82 | 375 | 48 | 3.6 | 0.07 |
| W312N | 24 | 375 | 35 | 15 | 0.23 |
| W312D | 37 | 375 | 32 | 6 | 0.15 |
| L178S + W312N | 55 | 375 | 20 | 50 | 0.63 |

TABLE 1-continued

Fraction of aminolysis (fa) for carboxypeptidase Y and $S_1$ mutants in transpeptidation of a substrate having an argninine at $P_1$

| Enzyme | t (min) | [N] (mM) | S (%) | P (%) | fa |
|---|---|---|---|---|---|
| L178D + W312N | 83 | 375 | 25 | 57 | 0.71 |
| L178D + W312D | 43 | 375 | 31 | 49 | 0.71 |
| L245E + W312N | 6100 | 375 | 50 | 7 | 0.20 |

Reactions were performed with 2 mM substrate at pH 7.5
t = time of assay
[E] = 0.1 mg/mL.
N = nucleophile (H-Leu-NH$_2$)
S = substrate (Bz-G-A-R-A-R-A-OH),
P = product (Bz-G-A-R-A-R-L-NH$_2$) and
fa = fraction of aminolysis.

As can be seen from the low fraction of aminolysis obtained (fa=0.05), wild type carboxypeptidase Y did not efficiently catalyze transpeptidation of a peptide substrate having an arginine amino acid residue in $P_1$ with a leucine amide nucleophile. In contrast, substitution of alanine, serine or aspartic acid for leucine at position 178 or substituting asparagine or aspartic acid for tryptophan at position 312, resulted in a substantial increase in the fraction of aminolysis obtained. Substitution of a negatively charged amino acid residue such as glutamic acid for arginine at position 241 significantly increased the fraction of aminolysis obtained at a nucleophile concentration of 375 mM. Additionally, substitution of a negatively charged amino acid residue, such as glutamic acid, at position 245, also resulted in an increase in the fraction of aminolysis. Combination mutants which included substitutions at positions L178 and W312 or L245 and W312 also displayed a significant increase in fraction of aminolysis.

Example 2

Methods:

Site specific mutagenesis was performed as described for Example 1 to produce the $S_1'$ mutants used below.

Transamidation reactions were performed as described for Example 1.

TABLE 2

Fraction of aminolysis (fa) for transpeptidation of FA-Ala-Xaa-OH with H-Gly-NH using $S_1$ mutant carboxypeptidase Y

| | $P_1'$ of FA-Ala-Xaa-OH substrate | | | | |
|---|---|---|---|---|---|
| Enzymes | Ala | Val | Leu | Met | Phe |
| Wild type | 0.90 | 0.16 | 0.20 | 0.18 | 0.04 |
| T60A | 0.91 | 0.44 | 0.32 | 0.16 | 0.12 |
| T60V | 0.94 | 0.29 | 0.15 | 0.17 | 0.08 |
| T60L | 0.91 | 0.17 | 0.13 | 0.08 | 0.24 |
| T60F | 0.85 | 0.15 | 0.17 | 0.21 | 0.12 |
| T60W | 0.93 | 0.39 | 0.45 | 0.49 | 0.47 |
| T60M | 0.78 | 0.15 | 0.03 | 0.01 | 0.18 |
| T60C | 0.92 | 0.27 | 0.19 | 0.15 | 0.08 |
| T60Y | 0.90 | 0.43 | 0.66 | 0.58 | 0.51 |
| T60D | 0.87 | 0.53 | 0.25 | 0.15 | 0.15 |
| T60E | 0.82 | 0.33 | 0.05 | 0.07 | 0.02 |
| M398G | 0.93 | 0.42 | 0.59 | 0.83 | 0.66 |
| M398A | 0.93 | 0.65 | 0.84 | 0.89 | 0.84 |
| M398V | 0.93 | 0.81 | 0.91 | 0.83 | 0.86 |
| M398I | 0.93 | 0.87 | 0.91 | 0.83 | 0.75 |
| M398L | 0.96 | 0.81 | 0.88 | 0.71 | 0.27 |
| M398F | 0.87 | 0.83 | 0.85 | 0.86 | 0.85 |
| M398Y | 0.90 | 0.89 | 0.90 | 0.90 | 0.92 |

TABLE 2-continued

Fraction of aminolysis (fa) for transpeptidation of
FA-Ala-Xaa-OH with H-Gly-NH
using $S_1$ mutant carboxypeptidase Y

| Enzymes | P$_1$' of FA-Ala-Xaa-OH substrate | | | | |
|---|---|---|---|---|---|
| | Ala | Val | Leu | Met | Phe |
| M398C | 0.93 | 0.52 | 0.75 | 0.65 | 0.64 |
| M398N | 0.92 | 0.52 | 0.36 | 0.70 | 0.11 |
| M398E | 0.92 | 0.82 | 0.84 | 0.74 | 0.71 |
| M398R | 0.48 | 0.26 | 0.16 | 0.33 | 0.11 |
| T60F + M398F | 0.86 | 0.73 | 0.86 | 0.82 | 0.66 |
| T60A + M398L | 0.92 | 0.91 | 0.94 | 0.72 | 0.52 |
| T60Y + M398L | 0.92 | 0.89 | 0.95 | 0.93 | 0.87 |
| T60D + M398L | 0.89 | 0.90 | 0.89 | 0.66 | 0.62 |
| T60A + M398Y | 0.80 | 0.81 | 0.83 | 0.83 | 0.81 |
| T60Y + M398Y | 0.74 | 0.74 | 0.77 | 0.76 | 0.75 |
| T60D + M398Y | 0.70 | 0.71 | 0.75 | 0.72 | 0.56 |

Reaction conditions: 0.2 mM FA-Ala-Xaa-OH substrate, 1.9 M H-Gly-NH$_2$ nucleophile, 50 mM MEPES, 5 mM EDTA, pH 7.5, room temperature As can be seen from the data in Table 2, in transpeptidation reactions, wild type carboxypeptidase Y has a very strong and narrow preference for peptide substrates having alanine as a leaving group in the P$_1$' position. Substitution of an amino acid at positions T60 and M398 within the S$_1$' subsite of carboxypeptidase Y broadened the specificity of the carboxypeptidase, such that the fraction of aminolysis was increased for other amino acid residues as leaving groups (e.g., valine, leucine, methionine and phenylalanine). As can be seen from the Table, the various substitutions had differing effects on the fraction of aminolysis depending on the leaving group. For leucine as a leaving group, substitutions at position T60, such as T60A, T60W or T60Y were the most effective at increasing the fraction of aminolysis. Additionally, substitutions at position M398 had a more dramatic effect on fraction of aminolysis when leucine was the leaving group. Examples of substitutions at M398 that enhanced transpeptidation using carboxypeptidase Y and a substrate having leucine as a leaving group include M398A, M398V, M398, M398I, M398L, M398F, M398Y, M398C, M398N and M398E. Substitutions at both position T60 and M398 further improved the fraction of aminolysis for a substrate with leucine as a leaving group: T60F+M398F, T60A+M398L, T60Y+M398L, T60D+M398L, T60A+M398Y, T60Y+M398Y and T60D+M398Y.

Example 3

Methods:

Site specific mutagenesis was performed as described in Example 1 to produce the specific substitution mutants described below. Transamidation reactions were performed as described for Example 1.

In table 3, below, K$_{N(app)}$ represents the nucleophile concentration at which fa is half of the maximum value (a measure for the dissociation constant of the nucleophile). fa$_{max}$ is the highest possible fa obtained at saturation of the enzyme with the nucleophile.

TABLE 3

Transpeptidation of FA-Ala-OBzl with H-Leu-NH$_2$
using double substitution mutants.

| Enzyme | K$_{N(app)}$ (mM) | fa |
|---|---|---|
| Wild type | 0.98[b] | 0.95[a] |
| T60A | 1.1[c] | 0.92[a] |
| T60V | 1.2[b] | 0.97[a] |

TABLE 3-continued

Transpeptidation of FA-Ala-OBzl with H-Leu-NH$_2$
using double substitution mutants.

| Enzyme | K$_{N(app)}$ (mM) | fa |
|---|---|---|
| T60L | 2.3[c] | 1.0[b] |
| T60F | 0.75[b] | 0.98[a] |
| T60Y | 1.0[b] | 0.95[a] |
| T60W | 5.4[b] | 0.96[a] |
| T60C | 0.88[a] | 0.98[a] |
| T60M | 3.4[c] | 0.98[b] |
| T60D | 1.5[c] | 0.94[b] |
| T60E | 2.0[b] | 0.94[a] |
| M398G | 1.6[a] | 0.95[a] |
| M398A | 0.83[a] | 0.93[a] |
| M398V | 1.43[b] | 0.87[a] |
| M398I | 0.91[b] | 0.94[a] |
| M398L | 1.2[b] | 1.0[a] |
| M398F | 2.3[b] | 0.96[a] |
| M398Y | 5.2[c] | 0.78[b] |
| M398C | 0.74[b] | 0.95[a] |
| M398N | 1.2[c] | 0.83[a] |
| M398E | 0.93[a] | 0.97[a] |
| M398R | 9.9[c] | 0.39[b] |
| T60A + M398L | 1.0[b] | 0.99[a] |
| T60Y + M398L | 1.7[c] | 1.0[a] |
| T60D + M398L | 2.0[b] | 1.0[a] |
| T60A + M398Y | 9.1[b] | 0.97[a] |
| T60Y + M398Y | 5.4[b] | 0.99[a] |
| T60D + M398Y | 9.2[c] | 0.89[a] |

The standard deviation of values marked by [a] is ± 0 to 3% while [b] indicates a deviation of ± 3 to 10% and [c] indicates ± 10 to 30%. Substrate = FA-Ala-OBzl (0.2 mM) Nucleophile = H-Leu-NH$_2$ pH = 7.5

K$_{N(app)}$ indicates the concentration at which fa$_{max}$/2 is reached and thus describes the apparent binding constant of the nucleophile. Because the competing hydrolysis reaction is thought to occur while the leaving group remains attached to the to the acyl-enzyme intermediate, a low K$_{N(app)}$ is preferred.

In table 3, the following mutants displayed an increase in fa$_{max}$ while decreasing K$_{N(app)}$: T60F, T60C, and M398E. Other mutants, such as T60V, T60L, T60F, T60W, T60C, T60M, M398L, and M398F showed an increase in both fa$_{max}$ and K$_{N(app)}$.

Example 4

Methods:

Site specific mutagenesis was performed as described for Example 1 to generate the specific mutants described below. Transamidation reactions were performed as described for Examples 1.

TABLE 4

Transpeptidation of Bz-G-A-R-A-R-X-OH at pH 7.5
at 50% substrate consumption

| Enzyme | Leaving Group | t (min) | fa | P$_{max}$ |
|---|---|---|---|---|
| Wild Type | A | ca. 110000 | <0.05 | 0 |
| | V | nd | <0.05 | 0 |
| | I | nd | <0.05 | 0 |
| | M | nd | <0.05 | 0 |
| | L | nd | <0.05 | 0 |
| L178S | S | 790 | 0.65 | 0.38 |
| | A | 14 | 0.73 | 0.63 |
| | V | 40 | 0 | 0 |
| | I | 26 | 0 | 0 |
| | M | 28 | 0 | 0 |
| | L | 2.1 | 0.01 | 0.01 |

TABLE 4-continued

Transpeptidation of Bz-G-A-R-A-R-X-OH at pH 7.5 at 50% substrate consumption

| Enzyme | Leaving Group | t (min) | fa | $P_{max}$ |
|---|---|---|---|---|
| N51Q + L178S | A | 34 | 0.72 | 0.60 |
| | V | 194 | 0.62 | nd |
| | I | 211 | 0.62 | nd |
| | M | 211 | 0.51 | nd |
| | L | 23 | 0.20 | 0.18 |
| L178S + M398L | A | 41 | 0.77 | >0.48 |
| | V | 30 | 0.45 | nd |
| | I | 33 | 0.54 | nd |
| | M | 17 | 0.17 | nd |
| | L | 1 | 0.39 | >0.39 |
| N51Q + L178S + M398L | A | 24 | 0.87 | >0.67 |
| | V | 168 | 0.82 | nd |
| | I | 129 | 0.82 | nd |
| | M | 84 | 0.75 | nd |
| | L | 52 | 0.76 | >0.73 |
| T60Y + L178S + M398L | S | 3400 | 0.18 | 0.09 |
| | A | 1200 | 0.68 | 0.43 |
| | V | 1100 | 0.60 | 0.38 |
| | I | 460 | 0.72 | 0.53 |
| | M | 730 | 0.50 | 0.39 |
| | L | 360 | 0.72 | 0.53 |
| N51Q + M398L | A | 3200 | 0.18 | >0.07 |
| | V | nd | nd | nd |
| | I | nd | nd | nd |
| | M | nd | nd | nd |
| | L | 3500 | 0.10 | >0.04 |

Reaction conditions: 2 mM Bz-G-A-R-A-R-X-OH substrate; 375 mM H-Leu-NH$_2$ nucleophile [E] = 0.1 mg/mL, pH 7.5 $P_{max}$ = peak product yield The data in table 4 demonstrates that the rate of transpeptidation of a substrate was affected by the nature of the leaving group. Substitutions at positions N51 and M398, within the S$_1$' subsite, enhanced transpeptidation for a particular leaving group. For example, the fraction of aminolysis for leucine as a leaving group was improved with the following mutants: T60Y+L178S+M398L and N51Q+L178S+M398L. Additionally, peak product yield was enhanced by substitutions at positions L178, M398, N51 or T60Y, from 0, with a wild type mutant. L178S contains a mutation in S$_1$. When combined with substitutions in S$_1$', such as M398L or T60Y and M398L or N51Q and M398L, the fraction of aminolysis obtained with leucine as a leaving group was greatly enhanced, from 0.01 to 0.39, 0.71 and 0.76, respectively. Additionally, there was a corresponding increase in the peak product yield from 0.01 to 0.39, 0.53 and 0.73, respectively.

Example 5

Methods:

Site specific mutagenesis was performed as described for Example 1 to generate the specific mutants described below. Transamidation reactions were performed as described for Example 1.

TABLE 5

Transpeptidation of BZ-G-A-R-A-R-X-OH at pH 6.5 at 50% substrate consumption

| Enzyme | Leaving Group | t (min) | fa | $P_{max}$ |
|---|---|---|---|---|
| L178S | S | 108 | 0.34 | 0.63 |
| | A | 34 | 0.79 | 0.74 |
| | L | 17 | 0.03 | 0.03 |

TABLE 5-continued

Transpeptidation of BZ-G-A-R-A-R-X-OH at pH 6.5 at 50% substrate consumption

| Enzyme | Leaving Group | t (min) | fa | $P_{max}$ |
|---|---|---|---|---|
| N51Q + L178S | A | 31 | 0.87 | 0.78 |
| | L | 19 | 0.28 | 0.26 |
| L178S + M398L | A | 53 | 0.92 | 0.48 |
| | L | 19 | 0.54 | 0.54 |
| N51Q + L178S + M398L | A | 194 | 0.91 | 0.70 |
| | L | 36 | 0.84 | 0.80 |
| T60Y + L178S + M398L | A | 540 | 0.70 | 0.49 |
| | L | 270 | 0.60 | 0.51 |
| N52Q + T60Y + L178S + M398L | A | 1900 | 0.77 | 0.72 |
| | L | 780 | 0.65 | 0.57 |

Reaction conditions: 2 mM Bz-G-A-R-A-R-X-OH substrate, 750 mM H-Leu-NH$_2$, nucleophile, [E] = 0.1 mg/mL, pH 6.5
$P_{max}$ = peak product yield The data in Table 5 indicates that the fraction of aminolysis obtained is enhanced at pH 6.5 (as compared to pH 7.5, in Table 4) for carboxypeptidase mutants containing substitutions within S$_1$ and S$_1$' subsites. For example, with leucine as a leaving group, the fa for mutant N51Q+L178S increased from 0.20 to 0.28, and $P_{max}$ increased from 0.18 to 0.26.

Example 6

Methods:

Site specific mutagenesis was performed as described for Example 1 to generate the specific mutants described below. Transamidation reactions were performed as described in the previous examples.

TABLE 6

Transamidation of Bz-G-A-R-A-R-A-OH and FA-Arg-Ala-OH Substrate [S] = 2 mM

| | Bz-G-A-R-A-R-A-OH | | | FA-Arg-Ala-OH | | |
|---|---|---|---|---|---|---|
| Enzyme | fa | t½ | $P_{max}$ | fa | t½ | $P_{max}$ |
| L178S | 0.77 | 66 | 0.61 | 0.89 | 32 | 0.76 |
| L178S + M398L | 0.91 | 85 | nd | .99 | 26 | 0.90 |
| N241D | 0.15 | 168 | 0.09 | 0.85 | 2100 | 0.56 |
| N241D + W312N | 0.17 | 97 | 0.13 | 0.74 | 82 | 0.58 |
| N241D + W312A | 0.28 | 76 | 0.20 | 0.80 | 21 | 0.72 |
| N241D + W312L | 0.05 | 28 | 0.05 | 0.50 | 11 | 0.37 |
| N241D + W312F | 0.24 | 40 | 0.17 | 0.70 | 73 | 0.58 |
| N241E | 0.47 | 200 | 0.25 | 0.92 | 62 | nd |
| N241E* | 0.43 | 94 | 0.25 | 0.70 | 900 | 0.49 |
| L245E | 0.20 | 610 | 0.09 | 0.83 | 88 | 0.73 |
| W312D | 0.16 | 170 | 0.08 | 0.77 | 68 | 0.67 |

*[S] = 0.2 mM
Nucleophile = H-Leu-NH$_2$
[N] = 375 mM,
pH = 7.5
[E] = 0.1 mg/mL

For transpeptidation of a peptide substrate having a positively charged P$_1$ amino acid residue, such as arginine, substitution of an amino acid residue in both an S$_1$ (L178S) and S$_1$' (M398L) subsite resulted in a significant increase in both the fraction of aminolysis obtained and the peak product yield for a substrate having a positively charged amino acid residue at P$_1$. Additionally, substitution of a negatively charged amino acid residue, such as aspartic acid or glutamic acid, in an S$_1$ subsite, such as N241, L245 or W312, also resulted in an increase in fa and $P_{max}$.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A method for transamidating a peptide substrate having a $P_1$ amino acid residue with a positively charged side chain and a $P_3$ amino acid residue with a positively charged side chain, the method comprising:

reacting the peptide substrate with a nucleophile in the presence of a modified carboxypeptidase Y, wherein the modified carboxypeptidase comprises at least one substitution in an $S_1$ subsite with an amino acid having a negatively charged side chain and at least one substitution of an amino acid residue capable of interacting with a peptide substrate $P_3$ residue wherein the substitution introduces an amino acid having a negatively charged side chain wherein at least one substitution in the $S_1$ subsite and at least one substitution of an amino acid residue capable of interacting with a peptide substrate $P_3$ residue are different.

2. The method of claim 1, wherein the modified carboxypeptidase comprises at least one substitution in the $S_1$ subsite at amino acid residue L178, W312, N241, or L245.

3. The method of claim 2, wherein at least one of L178, W312, N241, or L245 is replaced by aspartic acid or glutamic acid.

4. The method of claim 1, wherein the nucleophile comprises an amino acid ester or amino acid amide.

5. The method of claim 4, wherein the nucleophile comprises Leu-OH, Leu-OR, or Leu-NRR'.

6. The method of claim 1, wherein the modified carboxypeptidase further comprises at least one substituted amino acid residue in an $S_1$ or $S_2$ subsite.

7. The method of claim 1, wherein the modified carboxypeptidase further comprises at least one substitution in an $S_1$' subsite selected from the group consisting of N51Q, T60W, T60Y, T60A M398L, M398G M398A, M398V, M398I, M398F, M398Y, M398C, M398N, and M398E.

8. The method of claim 7, wherein the modified carboxypeptidase comprises at least two amino acid substitutions in the $S_1$' subsite.

9. The method of claim 8, wherein the at least two amino acid substitutions in the $S_1$' subsite include a substitution at position T60 and a substitution at position M398.

10. The method of claim 9, wherein the substitution at position T60 is T60F, T60L, T60Y, or T60D.

11. The method of claim 9, wherein the substitution at position M398 is M398F, M398L, or M398Y.

12. The method of claim 1, wherein the modified carboxypeptidase further comprises at least one substitution of an amino acid in an $S_2$ subsite.

13. The method of claim 12, wherein the substitution in the $S_2$ subsite is in at least one of positions E296, S297, or N303.

14. The method of claim 12, wherein the substitution in the $S_2$ subsite is E296F, S297A, N303A, or N303F.

15. The method of claim 12, wherein the peptide substrate includes an Ala residue at $P_2$.

16. The method of claim 1, wherein the modified carboxypeptidase Y includes a substitution of an amino acid residue capable of interacting with a peptide substrate $P_3$ residue in at least one of positions N241, N242, L245, and A246.

17. The method of claim 1, wherein reacting is at about pH 6.3 to about pH 6.7.

18. A modified carboxypeptidase Y, comprising at least one substitution in an $S_1$ subsite with an amino acid having a negatively charged side chain and at least one substitution of an amino acid residue capable of interacting with a peptide substrate $P_3$ residue wherein the substitution introduces an amino acid having a negatively charged side chain wherein at least one substitution in the $S_1$ subsite and at least one substitution of an amino acid residue capable of interacting with a peptide substrate $P_3$ residue are different.

19. The modified carboxypeptidase of claim 18, further comprising at least one substituted amino acid residue in an $S_1$ or $S_2$ subsite.

20. The modified carboxypeptidase of claim 18, further comprising a substituted amino acid residue in at least one of positions L178 and W312.

21. The method of claim 1, wherein the peptide substrate includes an Ala residue at $P_2$.

22. The method of claim 16, wherein the modified carboxypeptidase Y comprises at least one substitution selected from the group consisting of N241D, N241E, N242D, N242E, L245D, L245E, A246D and A246E.

23. The method of claim 1, wherein the peptide substrate includes a C-terminal sequence selected from the group consisting of GRF (1-43)-Xaa (SEQ ID NO:1), GLP 1 (1-36)-Xaa (SEQ D) NO:2), and GLP 1 (7-36)-Xaa (SEQ ID NO.3), wherein the Xaa is an amino acid residue.

24. The modified carboxypeptidase of claim 18, wherein at least one substitution in the $S_1$ subsite is at amino acid residue L178, W312, N241, or L245.

25. The modified carboxypeptidase of claim 18, wherein at least one substitution of an amino acid residue capable of interacting with a peptide substrate $P_3$ residue is at least one of positions N241, N242, L245, and A246.

26. The method of claim 16, wherein at least one of N241, N242, L245, or A246 is replaced by aspartic acid or glutamic acid.

27. The modified carboxypeptidase of claim 24, wherein at least one of N241 and L245 is replaced by an aspartic acid or glutamic acid residue.

28. The modified carboxypeptidase of claim 25, wherein at least one substitution of an amino acid residue capable of interacting with a peptide substrate $P_3$ residue is selected from the group consisting of N242D, N242E, A246D and A246E.

* * * * *